(12) United States Patent
Chiou

(10) Patent No.: US 8,846,646 B2
(45) Date of Patent: Sep. 30, 2014

(54) TOPICAL TREATMENT OF SKIN INFECTION

(75) Inventor: Win L Chiou, Burr Ridge, IL (US)

(73) Assignee: Winlind Skincare, LLC, Burr Ridge, IL (US)

( * ) Notice: Subject to any disclaimer, the term of this patent is extended or adjusted under 35 U.S.C. 154(b) by 789 days.

(21) Appl. No.: 12/244,924

(22) Filed: Oct. 3, 2008

(65) Prior Publication Data

US 2010/0087403 A1   Apr. 8, 2010

(51) Int. Cl.
*A61K 31/047* (2006.01)
*A61K 31/765* (2006.01)
*A61K 47/10* (2006.01)
*A61K 31/60* (2006.01)
*A61K 9/00* (2006.01)

(52) U.S. Cl.
CPC ........... *A61K 9/0014* (2013.01); *A61K 31/60* (2013.01); *A61K 31/765* (2013.01); *A61K 47/10* (2013.01); *Y10S 514/852* (2013.01); *Y10S 514/859* (2013.01); *Y10S 514/863* (2013.01); *Y10S 514/884* (2013.01); *Y10S 514/944* (2013.01); *Y10S 514/941* (2013.01)
USPC ........... 514/164; 514/738; 514/852; 514/859; 514/863; 514/772.4; 514/884; 514/944; 514/941; 424/682

(58) Field of Classification Search
CPC . A61K 2300/00; A61K 31/60; A61K 31/765; A61K 47/10; A61K 9/0014; A61K 9/0043
USPC ............. 514/859, 164, 738, 159, 492, 772.4, 514/852, 863, 884, 941, 944; 424/682
See application file for complete search history.

(56) References Cited

U.S. PATENT DOCUMENTS

| | | | |
|---|---|---|---|
| 4,767,750 A | | 8/1988 | Jacquet |
| 4,883,660 A | * | 11/1989 | Blackman et al. ............ 514/171 |
| 5,525,635 A | | 6/1996 | Moberg |
| 5,549,888 A | | 8/1996 | Venkateswaran |
| 5,569,651 A | * | 10/1996 | Garrison et al. ............. 514/159 |
| 5,667,790 A | | 9/1997 | Sellers, Jr. |
| 5,753,637 A | * | 5/1998 | Fried ............................. 514/161 |
| 6,455,065 B1 | | 9/2002 | Hymes |
| 6,616,923 B1 | | 9/2003 | Chiou et al. |
| 7,258,875 B2 | | 8/2007 | Chiou |
| 2010/0087403 A1 | | 4/2010 | Chiou |
| 2010/0203107 A1 | | 8/2010 | Koo et al. |

OTHER PUBLICATIONS

International patent application PCT/US2009/058607 International Search Report mailed May 6, 2010.
Carreira, C. M. et al "Antimicrobial effect of intracanal substances" Journal of Applied Oral Science, 2007, 15(5), 453-458.
Chirife, J. et al "In vitro antibacterial activity of concentrated polyethylene glycol solutions" Antimicrobial Agents and Chemotherapy, 1983, 24(3), 409-412.
Rodan & Fields, Proactiv Solution: Take action today; Three Simple Steps to a clearer tomorrow, (Brochure was received by mail upon request in early 2008).
AcneFree Severe with Time-Released 10% Benzoyl Peroxide & Retinol; University Medical Pharmaceuticals, (Brochure are photocopies of their outside package purchased from a local drug store in Sep. 2008).
Clean & Clear advantage acne control kit, Johnson & Johnson, (Brochure are photocopies of their outside package purchased from a local drug store in Sep. 2008).
Ak Gupta et al.: Rosacea and its management: an overview; JEADV (2005) 19, 273-285.
Hand book of Nonprescription Drugs; An Interactive Approach to Self-Care, 13th Edition; Section VIII, Dermatologic Disorder, Chapter 32, ACNE (2002).
A. Katsambas et al.: New and emerging treatments in dermatology: acne; Dermatologic Therapy, vol. 21, 2008, 86-95; ISSN 1396-0296.
International Cosmetic Ingredient Dictionary and handbook, Tenth Edition, 2004, vol. 2.
International Preliminary Report issued Apr. 5, 2011 in the corresponding International Application No. PCT/US2009/058607.

* cited by examiner

*Primary Examiner* — Savitha Rao
(74) *Attorney, Agent, or Firm* — Merchant & Gould P.C.

(57) ABSTRACT

The invention relates to an unexpected discovery that propylene glycol is highly effective at killing or inhibiting *Propionibacterium acnes* in a mammalian skin disorder, as well as to the use of propylene glycol and salicylic acid in a skin-disorder treatment. This invention also relates to compositions containing propylene glycol alone or in combination with salicylic acid for use in killing or inhibiting *Propionibacterium acnes*.

15 Claims, No Drawings

TOPICAL TREATMENT OF SKIN INFECTION

FIELD OF THE INVENTION

The invention relates to an unexpected discovery that propylene glycol is highly effective at killing or inhibiting *Propionibacterium acnes* in a mammalian skin disorder, as well as to the use of propylene glycol and salicylic acid in a skin-disorder treatment. This invention also relates to compositions containing propylene glycol alone or in combination with salicylic acid for use in killing or inhibiting *Propionibacterium acnes*.

BACKGROUND OF THE INVENTION

Acne is a common skin disorder. Many topical and systemic treatment methods are available ("Handbook of Nonprescription Drugs," American Pharmaceutical Association, 2002, pages 777-791; Katsambas and Dessiniot, Dermatologic Therapy, 21:86-95, 2008). A major shortcoming of the current treatment methods is their slow response often requiring several months of daily application or administration. Furthermore, satisfactory results achieved are often only about 40% to 60% (Chiou, 2007, U.S. Pat. No. 7,258,875 B2). Multiple (3 to 4) treatment steps are often required. Skin dryness and irritation are common; pitting or scarring may occur after treatment. Serious adverse effects can also occur for potent drugs. Although natural polyvalent metal compounds are recently employed to treat acne (Chiou, 2007, U.S. Pat. No. 7,258,875 B2), the stickiness of products due to the glycerin and thickening agent employed is a major drawback not acceptable by many patients in spite of their efficacy (unpublished observation). This is also the case in treating rosacea (Chiou, 2007, U.S. Pat. No. 7,258,875 B2).

The above review indicates a need to develop a new, cosmetically-acceptable, simple, one-step, highly safe and highly effective method for topically treating acne and rosacea without scarring and pitting. Ideally, the new drug treatment may not require a prescription and the same preparation can be used to treat both disorders. The present invention is aimed to achieve the above objectives. This is made possible by a surprising discovery that a commonly used, highly safe and rapidly absorbed (unpublished observation) compound possesses a strong in vitro bactericidal activity against *Propionibacterium acnes*, that is mainly responsible for the infection in acne. Many other factors are known to contribute to the occurrence of acne and vastly different approaches have been used to tackle the acne disorder. Interestingly, the same compound can also be used to treat infection in rosacea.

SUMMARY OF THE INVENTION

Propylene glycol (PG) is a colorless, odorless, sweet, light liquid. It has been widely employed for almost a century in skin-care products as a solvent, humectant, skin-conditioning agent and viscosity-decreasing agent ("International Cosmetic Ingredients Dictionary and Handbook", 2004, page 1536). It is listed as an inactive ingredient in dermatological drugs approved for marketing to date. The concentrations used generally are low ranging from about one to several percent.

The present invention discloses a very surprising, novel discovery that high concentrations of PG in vitro can very effectively kill *P. acnes* (Example 1), and without the need for any special prior cleansing or treatment, high (such as 20% to 80% by weight) aqueous PG solutions can virtually heal various sizes of infectious (pustular or papular) acne in about 0.5 to 2-3 days after one to several topical applications without pitting and scarring (Examples 2-4). No adverse effects were observed for solutions containing up to 75% or 80% PG (Examples 3-7). Pure (100%) PG and 90% PG solutions (Example 5) caused no noticeable adverse effects on normal skin (Example 5). Daily use of the 75% or 80% PG solution showed excellent prophylactic effect against new acne formation (Example 4). An aqueous solution containing 75% PG and 0.5% salicylic acid was highly effective against acne and rosacea without adverse reactions (Example 6).

Therefore, the present invention provides a highly effective, highly safe, novel method for killing and inhibiting *P. acnes* in mammalian skin disorder comprising topically applying a therapeutically effective amount of PG alone or in combination with a therapeutically effective amount of salicylic acid or other anti-acne compounds in a pharmaceutically acceptable dosage form to the area of skin disorder; one such skin disorder is acne. The above approach is also highly effective in treating rosacea.

Therefore, the present invention provides a very novel, simple, one-step and extremely effective and safe method for treating acne and rosacea comprising topically applying a therapeutically effective amount of PG alone or in combination with a therapeutically effective amount of salicylic acid or other anti-acne or anti-rosacea compounds in a dosage form to the area of skin lesion. The rationale and advantages of the novel combination of PG and salicylic acid will be discussed below.

DETAILED DESCRIPTION OF THE INVENTION

As used herein, the word "treatment" or "treating" includes killing and/or inhibiting *P. acnes* in skin, ameliorating or resolving the symptoms of, or healing, and preventing the development of acne or rosacea in mammals. It also may include helping or potentially helping ameliorate or resolve the symptoms of, cure or heal and prevent the development of acne or rosacea breakouts. It also may include the anti-acne or anti-rosacea effect or management. The phrase "effective amount" refers to that amount of PG or salicylic acid, which is sufficient for effective treatment when administered topically to any mammal in need of such treatment. The word "prevention" refers to prophylaxis. The phrase "dosage form" refers to, but is not limited to, the following: a liquid solution or mixture, suspension, gel, lotion, emulsion, paste, cream, spray or a medicated bandage, pad or mask. The method to prepare a dosage form is based on standard principles and methods described in various pharmaceutical literature. The phrase "salicylic acid" refers to salicylic acid or salicylate.

Concentrations of PG and other ingredients described in this application are all based on weight. The effective concentration of PG may range from about 5% to about 100%, about 8% to about 100%, about 10% to about 100%, about 15% to about 100%, about 20% to about 100%, about 25% to about 100%, about 50% to about 100%, about 10% to about 90%, about 15% to about 90%, and about 20% to about 90%, or preferably from about 25% to about 85% or from about 50% to about 90%. Use of pure (100%) PG is expected to produce the most dramatic effect of killing *P. acnes*. However, it may cause some minor skin irritation to the lesion of acne or to sensitive skin. Inclusion of some glycerin such as 5% to 20% soothes the skin and eliminates the itching and tingling caused by PG (Example 2).

The dosage form used may include a suitable amount of water, glycerin, other solvent(s), electrolyte(s), pH modifier(s), surfactant(s), absorption enhancer(s), emulsifier(s), thickener(s), fragrant(s), preservative(s), or a mixture thereof.

Although not required, the dosage form may also include one or more optional or additional anti-acne ingredients, including but not limited to salicylic acid, salicylate, benzoyl peroxide, metronidazole, erythromycin, tetracyclines and their derivatives, macrolides, clindamycin, minocycline, mecloycline, cloxycycline, azithromycin, clarithromycin, retinoids, azelaic acid, polyvalent metal compounds, picolinic acids, dapsone, anti-inflammatory compounds and astringents or a mixture thereof.

Salicylic acid is a Food-and-Drug-Administration-approved over-the-counter drug for treating acne because of its comedolytic property. This, and benzoyl peroxide, an anti-*P. acnes* drug, and many other ingredients (up to 30 or more) are often employed to form a 3- or 4-step treatment regime for acne. Skin dryness and irritation is a known problem associated with the above regime.

The novel combination of the PG and salicylic acid in a liquid solution in the present invention offers many unique and important advantages such as high efficacy for both infectious (pustular or papular) and non-infectious (whiteheads and blackheads in Example 6) components of acne, very low potential for allergic and adverse effects (both compounds being natural compounds), soothing, moisturizing, smoothing and firming effect on skin (Example 7), causing no pitting and scarring, a simple one-step method or a simple "all-in-one" method, great convenience for travelers (not carrying 3 or 4 bottles) and apparent economy. Furthermore, it can be used for rosacea treatment (Example 7). The present invention may also be useful to treat other bacterial skin infections. The concentration of salicylic acid or salicylate may range from about 0.05% to about 2% or from about 0.05% to about 3% or about 0.05% to about 6%. The dosage form may include glycerin ranging from about 5% to about 20% for skin-soothing effect (Example 2).

For killing or inhibiting *P. acnes* or for treating acne or rosacea breakouts, dosage preparation can be applied as thin layers up to several times a day to the area of lesions or prophylactically to the area that may have new breakouts later.

Therefore, the present invention provides a novel method for treating acne and rosacea comprising topically applying a therapeutically effective amount of propylene glycol in the absence or presence of a therapeutically effective amount of salicylic acid or other anti-acne or anti-rosacea compounds in a pharmaceutically acceptable dosage form to the area of lesion of acne or rosacea.

The present invention is illustrated by the following non-limiting examples.

Example 1

20% and 65% PG in Water for In Vitro Time-Kill Studies

An aqueous solution containing 20 or 65% PG was prepared by mixing PG and water in a proper proportion for the standard time-kill study using *Propionibacterium acnes* ATCC #6919. For the 20% PG solution 47% and 98% of the bacteria were killed at one and five hours, respectively. For the 65% PG solution 91% and 99.6% of the bacteria were killed at one in and five hours, respectfully. The initial bacteria count was $1.78 \times 10^6$ CFU/mL. Much higher PG solutions are expected to produce much higher killing rates.

Example 2

80% PG in Water for Acne Treatment: A Dramatic Effect

The above aqueous PG solution was directly applied as thin layers to several infectious papular acnes in the forehead of an adult. The infection (inflammation) appeared to completely disappear in 8 hours indicating a virtual healing only after one application. On another day, a larger papular acne was also practically healed in about 8 hours after only one application without scarring and pitting. Mild itching and tingling lasting about three minutes occurred in both studies. These minor adverse effects were totally avoided when some glycerin (about 10%) was added to the mixture. No special cleansing of the lesion or skin is required for all the studies described here and below, hence it is a truly simple one-step method or "all-in-one" method.

Example 3

20%, 40% and 60% PG in Water for Acne Treatment

The above PG solutions were used to treat papular and pustuler acnes on the face on different occasions in a subject. Complete healing was achieved after several applications in 2 to 3 days without pitting and scarring. No itching or tingling occurred.

Example 4

75% or 80% PG Solution for Acne Treatment: A Dramatic Prophylactic Effect

An aqueous solution containing 75% PG was employed to successfully treat various sizes of pastular and papular acnes in 4 adults. Daily applications were also performed in two adults for about one month without any side effects and with a clear sign of completely inhibiting new infectious acne formation indicating an excellent prophylactic effect. This was also the case with an 80% PG solution containing about 10% of glycerin.

Example 5

Daily Application of 90% PG or 100% PG in Adults without Acne

Pure (100%) PG or 90% PG in water was applied repeatedly to the normal skin of face and arm in 2 adults for several days. No adverse reactions were observed.

Example 6

75% PG-0.5% Salicylic Solution for Treatment of Rosacea and Acne

The above PG-salicylic acid solution was applied twice a day to the area of rosacea lesion in one subject and satisfactory results to quickly control breakouts and redness were obtained. The solution was also used to very successfully treat acne in two subjects without any adverse effects. Furthermore, the solution was highly effective against whiteheads and slower in response against blackheads; a higher salicylic acid concentration should be more efficacious. The PG is an excellent solvent for salicylic acid in this preparation.

Example 7

Tissue-Healing and Skin Firming Properties of PG

In all the studies conducted, PG solutions resulted in rapid healing of acne lesions without pitting and scarring. Furthermore, the applied areas of skin became smoother and firmer after about one month of daily use. These results indicate a tissue-healing and tissue-growth-promoting property of PG that is similar to the skin-firming phenomenon observed with a similar type of compound, glycerin (Chiou et al., U.S. Pat. No. 6,616,923, B1; unpublished observations).

It is to be understood that the above descriptions are intended to be illustrative, and not restrictive. One skilled in the art will be able to ascertain, without any more routine experimentation, many reference to specific embodiments described herein. These equivalents are intended to be encompassed by the following claims.

What is claimed is:

1. A method for treating acne, which consists of:
topically applying a composition to the skin of a subject in need thereof,
wherein the composition comprises:
an anti-acne agent consisting of an anti-acne effective amount of propylene glycol ranging from about 20% to about 100% by weight, and
a pharmaceutically acceptable medium;
wherein the composition is selected from the group consisting of a liquid solution, a liquid mixture, a suspension, a lotion, an emulsion, a paste, a gel, a cream, and a spray.

2. The method of claim 1, wherein the amount of propylene glycol ranges from about 50% to about 90% by weight.

3. The method of claim 1, wherein the amount of propylene glycol is about 60% by weight.

4. The method of claim 1, wherein the amount of propylene glycol is about 65% by weight.

5. The method of claim 1, wherein the amount of propylene glycol is about 75% by weight.

6. The method of claim 1, wherein the amount of propylene glycol is about 80% by weight.

7. The method of claim 1, wherein the pharmaceutically acceptable medium is selected from the group consisting of water, glycerin, other solvent, an electrolyte, a pH modifier, a surfactant, an absorption enhancer, an emulsifier, a thickener, a fragrance, a preservative, and combinations thereof.

8. The method of claim 1, wherein the acne is selected from the group consisting of pustular acne, papular acne, and combinations thereof.

9. A method for treating rosacea, which consists of:
topically applying a composition to the skin of a subject in need thereof,
wherein the composition comprises:
an anti-rosacea agent consisting of an anti-rosacea effective amount of propylene glycol ranging from about 20% to about 100% by weight, and
a pharmaceutically acceptable medium;
wherein the composition is selected from the group consisting of a liquid solution, a liquid mixture, a suspension, a lotion, an emulsion, a paste, a gel, a cream, and a spray.

10. The method of claim 1, wherein the amount of propylene glycol ranges from about 50% to about 90% by weight.

11. The method of claim 1, wherein the amount of propylene glycol is about 60% by weight.

12. The method of claim 1, wherein the amount of propylene glycol is about 65% by weight.

13. The method of claim 1, wherein the amount of propylene glycol is about 75% by weight.

14. The method of claim 1, wherein the amount of propylene glycol is about 80% by weight.

15. The method of claim 1, wherein the pharmaceutically acceptable medium is selected from the group consisting of water, glycerin, other solvent, an electrolyte, a pH modifier, a surfactant, an absorption enhancer, an emulsifier, a thickener, a fragrance, a preservative, and combinations thereof.

* * * * *